United States Patent [19]

Nunan

[11] 4,209,706
[45] Jun. 24, 1980

[54] FLUOROSCOPIC APPARATUS MOUNTING FIXTURE

[75] Inventor: Craig S. Nunan, Los Altos Hills, Calif.

[73] Assignee: Varian Associates, Inc., Palo Alto, Calif.

[21] Appl. No.: 915,086

[22] Filed: Jun. 12, 1978

Related U.S. Application Data

[63] Continuation of Ser. No. 745,154, Nov. 26, 1976, abandoned.

[51] Int. Cl.² .................................................. H01J 35/16
[52] U.S. Cl. .................................. 250/490; 250/522; 250/523
[58] Field of Search ................. 250/490, 439 R, 444, 250/445 R, 446, 523, 522

[56] References Cited

U.S. PATENT DOCUMENTS

| | | | |
|---|---|---|---|
| 2,818,510 | 12/1957 | Verse | 250/523 |
| 3,281,598 | 10/1966 | Hollstein | 250/523 |
| 3,500,045 | 3/1970 | Rossi | 250/445 |
| 3,617,749 | 11/1971 | Massiot | 250/523 |
| 3,670,163 | 6/1972 | Lajus | 250/523 |
| 3,868,506 | 2/1975 | Ogiso | 250/490 |

FOREIGN PATENT DOCUMENTS 1526087  3/1967  France .................................... 250/523

*Primary Examiner*—Craig E. Church
*Attorney, Agent, or Firm*—Stanley Z. Cole; Leon F. Herbert; Edward H. Berkowitz

[57] ABSTRACT

A mounting fixture provides rotational freedom in each of two orthogonal planes for motion of an X-ray source and diametrically opposed image intensifier. The relative positions of the X-ray source and image intensifier can be inverted by a simple 180° rotation about a third axis orthogonal to at least one of the two axes defined by the two rotational degrees of freedom.

7 Claims, 3 Drawing Figures

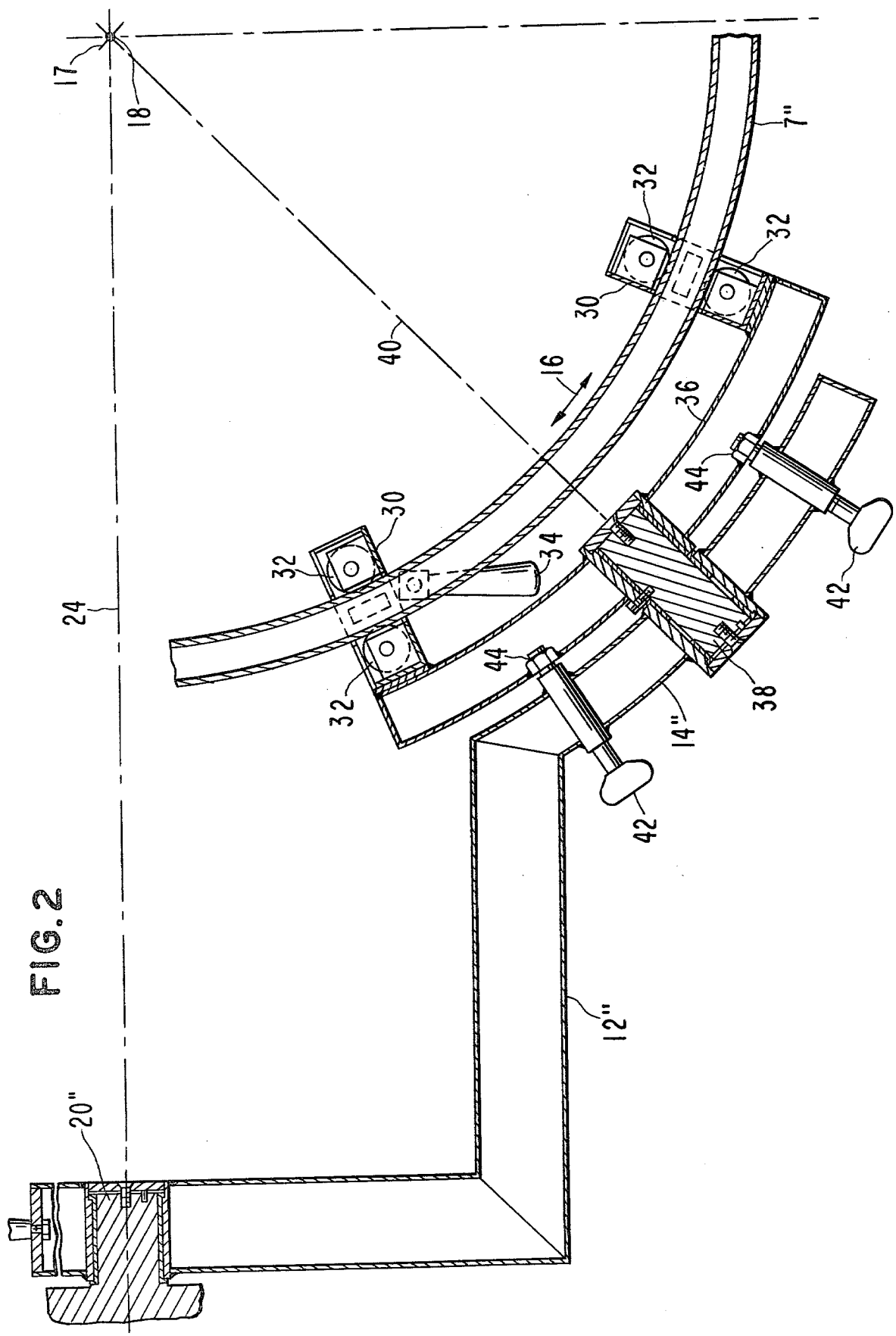

FLUOROSCOPIC APPARATUS MOUNTING FIXTURE

This is a continuation of application Ser. No. 745,154 filed 11/26/76 now abandoned.

BACKGROUND OF THE INVENTION

This invention is related to the structure of mounting fixtures for fluoroscopy apparatus.

DESCRIPTION OF THE PRIOR ART

Prior art mobile fluoroscopy apparatus has employed an X-ray source and an X-ray image intensifier in fixed axial relationship adapted to provide translational and rotational freedom. The fixed axial relationship may be regarded as defining a line segment directed from the X-ray source to the image intensifier, passing through the region of interest to be imaged. It will be useful to refer to this directed line segment or vector as describing the fixed relationship of X-ray source and image intensifier. With respect to the object to be imaged, the orientation of this directed line segment, or vector, is varied by adaptation of the mounting means for rotations vector about two orthogonal axes. For example, the X-ray source and image intensifier execute a coupled rotation along an arcuate path about a first axis providing rotational travel in the plane of this arc. Rotational travel ranging from 90° to 135° has been commonly employed. The entire arcuate path is freely rotatable about a second axis in the plane of the arc, passing through the object to be imaged and intercepting the aforementioned first axis at the isocenter. Apparatus wherein rotations are defined by axes intersecting at a common point are said to be isocentric. The prior art includes such apparatus as well as non-isocentric configurations. Discussion is referenced to isocentric apparatus for purposes of simplicity.

The X-ray source and image intensifier are mounted on a C-shaped member describing a substantial arc, for example, 180 degrees to accomodate the rotation of the source-to-image intensifier vector. The C-shaped member (C-arm) can slide in its mounting fixture, thus describing an orbital path about said first axis through the isocenter, but of course, the extent of this orbital motion is usually limited by interference of the X-ray source and/or image intensifier with parts of the mounting equipment. Rotation of the plane of the orbital motion is accomplished by pivoting the C-arm mounting fixture about said second axis through the isocenter whereby the orbital plane may be rotated through an arbitrary angle such as 360°. This second axis is usually the horizontal axis in ordinary practice.

Prior art mounting fixtures commonly possess an offset configuration with respect to the horizontal axis in order that the vector defined by the X-ray source and image intensifer can be made congruent with the horizontal axis.

Nonisocentrically mounted apparatus differs from isocentric apparatus in providing a greater variety of motions for the X-ray source-image intensifier vector. Whereas in isocentric equipment this vector is capable only of rotation about a point on the vector, in non-isocentric equipment rotation of the vector are available about external points, e.g., axes which do not intersect the vector, Such equipment can relocate the vector extreme to occupy points on a more complex surface, whereas in isocentric apparatus the source intensifer vector is constrained to define conjugate points on a sphere centered on the isocenter. An additional rotational degree of freedom (not germane to the present invention) is also provided for rotations of the entire mounting fixture about an axis perpendicular to the horizontal axis and displaced from the isocenter. This "scan" degree of freedom is often limited to angles of the order of ± (10 degrees-15 degrees).

It is important to the utility of this apparatus to provide for great flexibility in the positioning of the aforesaid vector. In a surgical environment, concurrent desiderata of the apparatus include the ability to approach the subject with the image intensifier from the non-sterile side of the subject, bringing the image intensifier close to the skin; and the ability to maintain the sterile area of the subject clear for the surgeon to function with maximum freedom. This has been partly accomplished with mechanical mounting structures offset as above described. Due to the asymmetry introduced thereby, the offset mount defines two distinguishable permutations in the mounting of the X-ray source and image intensifier. Consequently the sense of the source-intensifier vector is fixed with respect to the offset mount. A mere rotation by 180 degrees about the horizontal axis will not suffice to mutually transorm these permutations because the relationship of X-ray source, offset mounting fixture, and image intensifier remains invariant with respect to rotations (without regard to isocentric or non-isocentric properties of the apparatus). In principle, the transformation can be accomplished by physically removing the C-arm from the offset mounting fixture and remountig it in a reversed aspect, or alternatively, physically exchanging the positions of the X-ray source and the image intensifier on the C-arm. Either of these operations would be cumbersome and unsuitable at best. Two otherwise identical units may be employed; one having the travel of the X-ray source limited by the offset mount (standard configuration) and another having the image intensifer so limited (reversed configuration).

SUMMARY OF THE PRESENT INVENTION

The general object of the present invention is provision of means for reversing positions of collinearly opposed X-ray source and image intensifier detector on an apparatus so as to increase the range of orientations of the direction vector extending between the source and detector.

The objectives of the invention are accomplished by providing another rotational axis which is in the plane of the C-arm and is defined by a point on the offset mount and the center of orbital rotation, whereby the relationships of X-ray source and image intensifier may be inverted in the orbital center through rotation about said another axis.

The various features of the invention will become apparent by reference to the description and claims taken in conjunction with the accompanying drawings in which:

BRIEF DESCRIPTION OF THE DRAWINGS

FIG. 2 is a section of the mounting apparatus of the present invention.

DETAILED DESCRIPTION OF THE PREFERRED EMBODIMENT

Figure 1A:
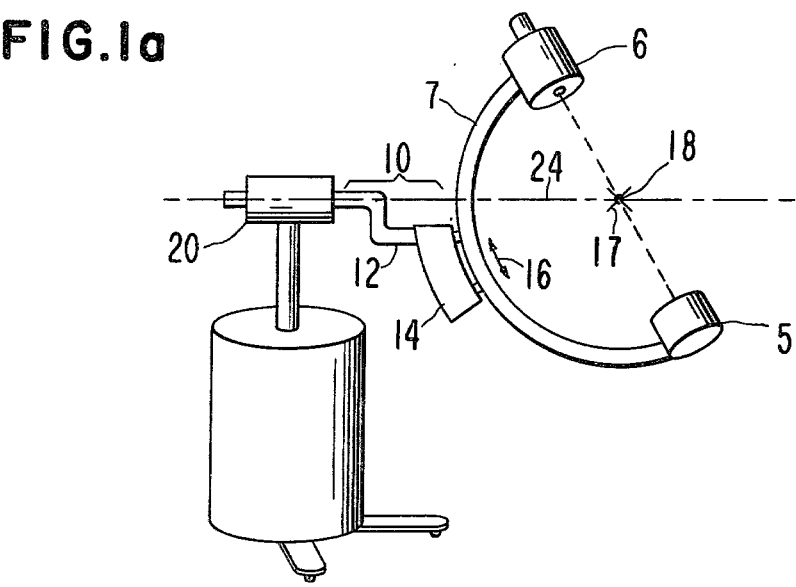
FIG. 1(a) is a schematic view of a standard configuration C-arm fluoroscopy apparatus of the prior art.
Figure 1B:
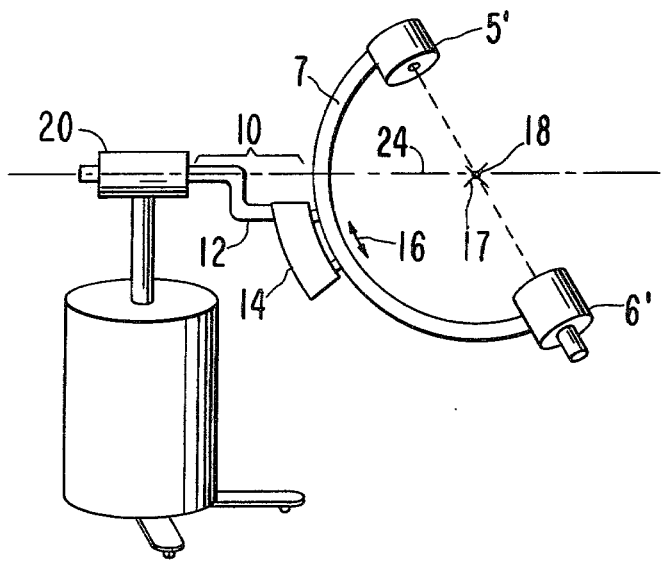
FIG. 1(b) is a schematic view of a reversed configuration C-arm fluoroscopy apparatus of the prior art.

The function accomplished by the structure of the present invention is best understood by reference to FIGS. 1(a) and 1(b) wherein two prior art configurations (of isocentric geometry) are shown. Each comprises an X-ray source 5 and 5' and an X-ray image intensification means 6 and 6', both mounted on the ends of an acurate member, or C-arm 7. The C-arm 7 is supported from a mounting fixture 10 which is characterized by an offset arm 12 and an arcuate portion 14. The arcuate portion 14 has a race, (not shown) in which C-arm 7 slideably engages thereby providing a rotational degree of freedom in the plane of the C-arm as indicated by arrows 16 about an axis 17 normal to the plane of the C-arm and passing through isocenter 18. Offset arm 12 is mounted on a supporting base 3 by means of a bearing 20. Bearing 20 permits mounting fixture 10 to rotate the plane of the C-arm 7 about axis 24 which is in the plane of the C-arm and passes through isocenter 18.

It will be observed that a 180 degree rotation about the axis 24 does not suffice to transform the apparatus of FIG. 1(a) into the apparatus of FIG. 1 (b). This is more clearly noted by observing that an asymmetry is introduced by offset arm 12. X-ray source 5' of FIG. 1(b) may be moved along the path shown by arrow 16 to occupy a position on horizontal axis 24 and proximate the mounting fixture portion 14, but image intensifier 6' cannot be manipulated to occupy that same location by rotation about axes 17 and 24. In other words, intensifier 6' can be moved around axis 17, to the left and upward as viewed in FIG. 1b, until it is proximate fixture portion 14, but subsequent rotation around axis 24 will find no location where intensifier 6' is on axis 24. Similarly X-ray image intensifier 6 of FIG. 1(a) may occupy a position on horizontal axis 24 proximate the mounting fixture 14, but X-ray source 5 cannot be manipulated to occupy that same location by rotations about the indicated axes.

The invention is most easily described in the context of isocentric geometry. Referring now to FIG. 2, a preferred embodiment of the instant invention, here employing isocentric geometry, comprises a mounting fixture comprising an offset arm 12" offsetting the fixture from axis 24, about which bearing 20" provides rotational freedom with respect to the axis 24. It should be understood that FIG. 2 is a view similar to FIG. 1(a) except that in FIG. 2 all elements are positioned in the plane of the paper and double prime numbers are used to designate the modified elements. C-arm 7" is engaged by race assemblies 30 including roller bearings 32 and is designed to provide at least 90 degrees rotation about axis 17. A locking mechanism (not shown) is actuated by lever 34 to seize the C-arm 7" and lock it in selected position along path 16.

Distinct from the prior art, the races 30 are not mounted directly upon the arcuate portion 14" of the mounting fixture. Instead, the races 30 are mounted on an intermediate arcuate arm 36, adapted to rotate via bearing 38 about an axis 40 with respect to arcuate portion 14". Locking means 42 are provided to secure intermediate arm 36 to arcuate portion 14" at discrete positions. For example, locking means 42 may assume the form of threaded pins 42 engaging threaded receiving means 44 in the intermediate arm 36.

It will be observed from FIG. 2 that the apparatuses mounted on the ends of C-arm 7" can be inverted in relative position with respect to the offset arm 12" by simple 180 degree rotation of intermediate arm 36 about axis 40. In this way not only are all pairs of conjugate points on the sphere defined by isocenter 18 and C-arm 7" accessible to the X-ray source and image intensifier, but also the sense of the relative position of the source and intensifier can be chosen for all points on this sphere by 180 degree rotation about axis 40.

One skilled in the art will recognize that variations of the present invention may be accomplished within the scope of the present disclosure. For example, to achieve simplicity, the preferred embodiment has been discribed in the context of an isocentric apparatus further characterized by an offset arm mounting geometry. While isocentric apparatus is desirable in many situations, non-isocentric apparatus employing an offset arm may equally employ the present invention to invert the sense of the X-ray source-image intensifier vector. Obviously examining media other than x-rays could be employed. For example, source 5 could be replaced by a source of penetrating ultrasonic waves, and intensifier 6 could be replaced by a detector of the ultrasonic waves. Accordingly, it is understood that changes may be affected in the particular embodiment above-described, which changes are within the scope of the appended claims.

What is claimed is:

1. An apparatus for examining an object, the apparatus comprising: a base member, a cantilever arm rotatably connected to said base, a retaining member said cantilever arm, a substantially C-shaped member rotatable within said retaining member, a source for creating an examining beam located at approximately one end of said C-shaped member, and a means for detecting said beam located at approximately the other end of said C-shaped member, said source and detecting means being positioned in opposing fashion thereby to form a beam vector in which said object may be imaged, said rotatable connections being rotatable one with respect to the others such that said object located within said beam vector can be totally spherically solid angle imaged without movement of said base or the object.

2. An apparatus according to claim 1 wherein said C-shaped member is slidably rotatable along a horizontal path within said retaining member.

3. An apparatus according to claim 2 wherein the rotatable connections of said apparatus are positioned such that they share a common mechanical iso-center of rotation within said beam vector and said object is a body or portion thereof.

4. An apparatus according to claims 2 or 3 wherein said cantilever arm is rotatably connected at approximately one of its ends to said beam by a first pivot means and said retaining member is rotatably connected at approximately the other end of said cantilever arm by a second pivot means, said cantilever arm offsetting the longitudinal axis of the first pivot means from the longitudinal axis of the second pivot means.

5. An apparatus according to claim 4 wherein the longitudinal axis of said first pivot means intersects the longitudinal axis of said second pivot means at an acute angle, and slidably rotatable movement of said C-shaped member within said retaining means intersects the longitudinal axis of said second pivot means, and wherein at said point of intersection, said movement is substantially perpendicular to the said axis of said second pivot means, the apparatus further including first locking means for releasably locking said retaining means against rotation about said second pivot means and second locking means for releasably locking said C-shaped member against slidable rotation within said retaining member.

6. An apparatus according to claim 5 wherein said first pivot means limits cantilever arm rotation to a movement at said pivot means which is perpendicular to the longitudinal axis of said first pivot means, said second pivot means limits retaining member rotation at said second pivot means to a movement perpendicular to the longitudinal axis of said second pivot means, and said retaining member limits said C-shaped member to substantially uniplanar sliding movement.

7. An apparatus according to claim 6 wherein the sliding rotation of said C-shaped member has an angular range of at least 90°.

* * * * *